United States Patent [19]

Takaoka et al.

[11] Patent Number: 5,004,824
[45] Date of Patent: Apr. 2, 1991

[54] FLUORINE-CONTAINING ORGANOSILICON COMPOUND

[75] Inventors: Akio Takaoka; Hiroshi Inomata, both of Takasaki, Japan

[73] Assignee: Shin-Etsu Chemical Co., Ltd., Tokyo, Japan

[21] Appl. No.: 372,528

[22] Filed: Jun. 28, 1989

[30] Foreign Application Priority Data

Jun. 29, 1988 [JP] Japan ................. 63-162172

[51] Int. Cl.$^5$ ................................. C07F 7/10
[52] U.S. Cl. ................................... 556/412
[58] Field of Search .......................... 556/412

[56] References Cited

U.S. PATENT DOCUMENTS 3,579,557  5/1971  Brooks et al. ................ 556/412

FOREIGN PATENT DOCUMENTS 58-142958  8/1983  Japan ................. 556/412
58-147483  9/1983  Japan ................. 556/412
58-147484  9/1983  Japan ................. 556/412

Primary Examiner—Paul F. Shaver
Attorney, Agent, or Firm—Foley & Lardner

[57] ABSTRACT

A novel fluorine-containing organosilicon compound represented by Formula (I):

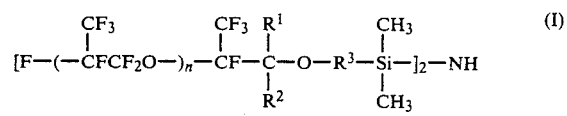

wherein n represents an integer of 0 or more, $R^1$ and $R^2$ may be the same or different and each represent a hydrogen atom or a fluorine atom, and $R^3$ represents an alkylene group having 1 to 6 carbon atoms.

This compound is useful as silica treatments, or surface treatments capable of imparting water repellency, oil repellency, etc. on the surface of glassware or the like.

2 Claims, 3 Drawing Sheets

FLUORINE-CONTAINING ORGANOSILICON COMPOUND

BACKGROUND OF THE INVENTION

1. Field of the Invention

This invention relates to a novel fluorine-containing organosilicon compound.

2. Description of the Prior Art

The fluorine-containing organosilicon compound provided in this invention is a substance hitherto unknown in the art.

SUMMARY OF THE INVENTION

An object of this invention is to originate a novel fluorine-containing organosilicon compound.

According to this invention, there is provided a fluorine-containing organosilicon compound represented by Formula (I):

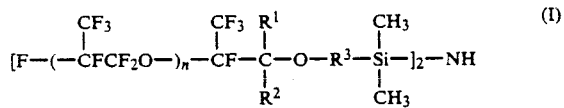

wherein n represents an integer of 0 or more, $R^1$ and $R^2$ may be the same or different and each represent a hydrogen atom or a fluorine atom, and $R^3$ represents an alkylene group having 1 to 6 carbon atoms.

The compound of this invention is useful as a treatment that treats an

group present on the surface of silica compounded into organic resins, silicone oil compositions, silicone rubbers, etc., as a protective agent that protects a

group in processes for the syntheses of pharmaceuticals, agricultural chemicals, etc., or as an adhesion improver that improves the adhesion of a resist or the like used in processes for the production of various semiconductor devices. It is also useful as a surface treatment that imparts water repellency, oil repellency and stainproofness to the surfaces of glasses such as optical lenses, spectacle lenses and glassware.

DETAILED DESCRIPTION OF THE INVENTION

Figure 1:
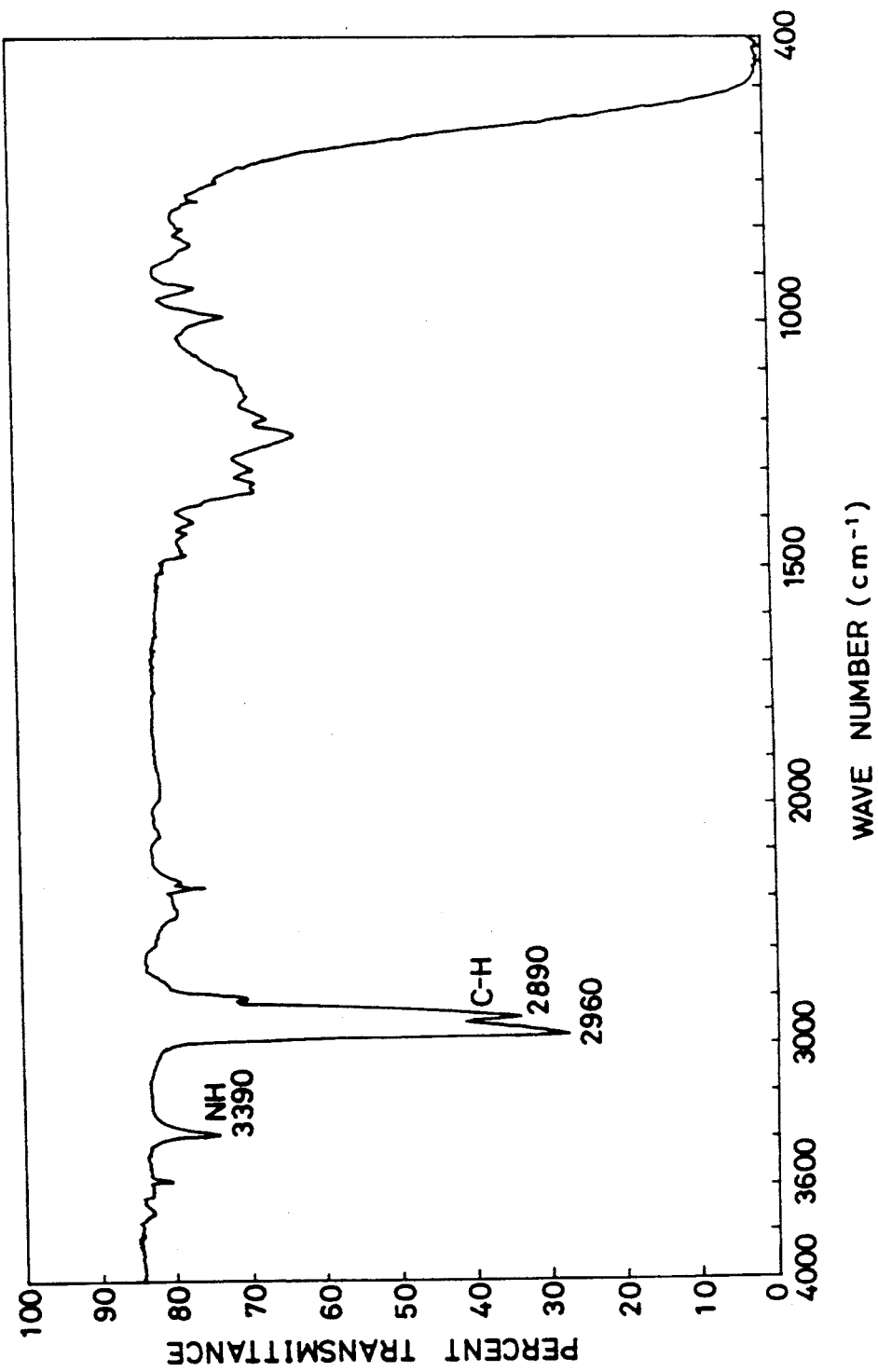
FIGS. 1 to 3 show infrared absorption spectra of the fluorine-containing organosilicon compound of this invention, obtained respectively in Examples 1 to 3.

In Formula (I) that represents the fluorine-containing organosilicon compound of this invention, the alkylene group represented by $R^3$, having 1 to 6 carbon atoms includes, for example, a methylene group, an ethylene group, a trimethylene group, a tetramethylene group, a pentamethylene group, and a hexamethylene group. It typically includes a trimethylene group and a tetramethylene group.

The n in Formula (I) represents an integer of 0 or more, usually of from 0 to 4, and typically from 1 to 4.

The fluorine-containing organosilicon compound of this invention can be prepared, for example, by reacting a fluorine-containing chlorosilane compound represented by Formula (II):

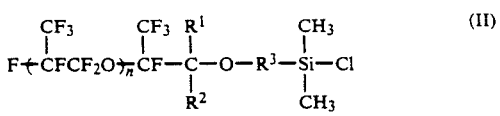

wherein $R^1$, $R^2$ and $R^3$ are as defined above, with ammonia under conditions described below.

Namely, the reaction is carried out preferably by slowly blowing ammonia gas into the fluorine-containing chlorosilane compound represented by Formula (II), and stopping the blowing of ammonia gas at the time an unreacted gas is recognized to have been generated. More preferably, it is carried out by dissolving the fluorine-containing chlorosilane compound in an inert solvent, slowly blowing ammonia gas into the solution in an amount of about 3/2 mol time the fluorine-containing chlorosilane compound, and stopping the blowing of ammonia at the time an unreacted gas is recognized to have been generated.

The above reaction may preferably be carried out by using solvents as exemplified by trichlorotrifluoroethane, hexane, dichloromethane, chloroform, carbon tetrachloride, diethyl ether, THF and dioxane in an amount of, for example, about 4 liter per mol of the fluorine-containing chlorosilane compound represented by Formula (II) and at a reaction temperature of from 0° to 100° C., and preferably from 20° to 50° C.

The fluorine-containing chlorosilane compound of Formula (II), usable as the starting material of the compound of Formula (I), can be prepared by the methods as disclosed, for example, in Japanese Pre-examination Patent Publications (KOKAI) Nos. 142958/1983, 147484/1983 and 167488/1983. More specifically, to make description taking as an example an instance in which $R^3$ is a trimethylene group, it can be prepared according to the following reaction process, using hexafluoropropylene oxide (HFPO) and dimethylchlorosilane as materials.

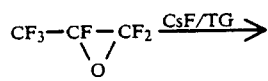

-continued

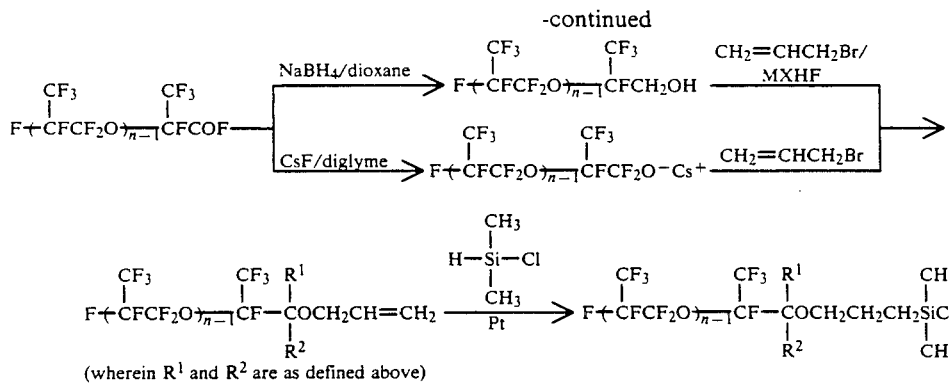

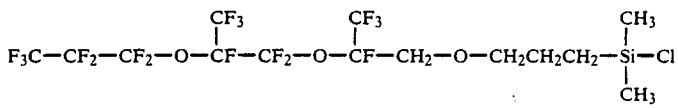

(wherein $R^1$ and $R^2$ are as defined above)

In the above reaction scheme, TG denotes tetraglyme, a solvent; MXHF, methaxylene hexafluoride used as a solvent; and TBAS, tetrabutyl ammonium hydrogen sulfate used as a catalyst.

In the above reaction, in the first reaction step in the CsF/TG system, the trimer of hexafluoropropylene oxide comes to hold a maximum proportion in the product under reaction conditions of, for example, an HFPO/CsF molar ratio of 103, a CsF/H$_2$O molar ratio of 2.83 (this water is used as a polymerization terminator), an HFPO feed rate of 1.57 g/min, and a feed time of 216 hours, in approximation. Under such reaction conditions, the product can be obtained in a yield of 93.5% and a distribution of oligomers formed, of 33.5% of dimers, 51.8% of trimers and 12.4% of tetramers. In the hydrosilylation reaction in which dimethylchlorosilane (DMCS) and a platinum catalyst are used (the instance where n=3, $R^1=R^2=H$ in the above reaction scheme), the reaction is carried out under conditions of, for example, a DMCS/allyl ether molar ratio of 1.47, a platinum/DMCS molar ratio of $3.6 \times 10^{-4}$, a reaction temperature of from 90° to 120° C. and a reaction time of 2 hours, and consequently the hydrosilylated product can be obtained in a yield of about 75%.

The fluorine-containing organosilicon compound of this invention can be also prepared by using primary amines as exemplified by methylamine, ethylamine, propylamine and butylamine, without limitation to the reaction of the fluorine-containing chlorosilane compound represented by the above Formula (II) with ammonium.

The fluorine-containing organosilicon compound of this invention has a perfluoroalkyl ether group in its molecule, and hence is useful as materials for imparting to the surfaces of articles, low surface energy properties, water repellency, oil repellency, release properties and so forth. In particular, it is useful as materials for imparting water repellency, oil repellency and stainproofness to the surfaces of glasses such as optical lenses, spectacle lenses and glassware, by treating the surfaces of these glasses by a known means such as spraying or dipping or by forming coatings on the surfaces.

EXAMPLES

This invention will be described below in greater detail by giving Examples and Comparative Examples.

EXAMPLE 1

In a reaction vessel with an internal volume of 1 liter, 300 ml of Freon-113 (CCl$_2$F-CClF$_2$) and 48.0 g (75 mmol) of a fluorine-containing organosilicon compound represented by the following formula:

$$F_3C-CF_2-CF_2-O-\underset{\underset{\displaystyle}{\overset{\displaystyle CF_3}{|}}}{CF}-CF_2-O-\underset{\underset{\displaystyle}{\overset{\displaystyle CF_3}{|}}}{CF}-CH_2-O-CH_2CH_2CH_2-\underset{\underset{\displaystyle CH_3}{|}}{\overset{\displaystyle CH_3}{|}}{Si}-Cl$$

were charged, and ammonia was blown into it for about 2 hours until unreacted ammonia was recognized in the reaction system, to carry out reaction under boiling and reflux. Thereafter, the reaction mixture was cooled to room temperature, and 5 ml of an aqueous 5N NaOH solution and 80 ml of water were added thereto to dissolve ammonium chloride suspended in the reaction mixture to separate the resulting reaction mixture into an aqueous layer and an organic layer. The organic layer separated was washed with water twice, followed by addition of magnesium sulfate to effect drying. Subsequently the solvent was removed and the resulting reaction product was subjected to distillation under reduced pressure to obtain 38.0 g of a compound as a fraction at a boiling point of 138° to 140° C./2 mmHg (yield: 85%). The resulting compound was subjected to elementary analysis and GC-MS analysis, and also infrared absorption spectrum and $^1$H-NMR spectrum were measured, to obtain the following results.

|  | Elementary analysis: | | | | |
| --- | --- | --- | --- | --- | --- |
|  | C | H | N | Si | F |
| Calculated*: (%) | 28.56 | 2.48 | 1.19 | 4.77 | 54.85 |
| Found: (%) | 28.41 | 2.53 | 1.12 | 4.69 | 54.55 |

(*as $C_{28}F_{34}H_{29}NO_6Si_2$)

GC-MS: m/e(M+) molecular weight: 1,177.
Infrared absorption spectrum:
As shown in FIG. 1, a peak derived from a —NH group was observed at a wave number of 3,390 cm$^{-1}$.
$^1$H-NMR spectrum: Solvent: Freon-113; external standard: TMS. δ (ppm): 3.80 (d, 4H, $J_{HF}$=12.0 Hz, 2×—CF—CH$_2$—O—) 3.35 (t, 4H, J=6.8 Hz, 2×—O—CH$_2$—CH$_2$—) 1.16 to 1.80 (m, 4H, 2×—CH- $_2$—CH$_2$—CH$_2$—) 0.23 to 0.63 (m, 4H, 2×—CH$_2$—Si) 0.00 (s, 12H, 2×Si(CH$_3$)$_2$).

From the above results, the compound obtained was found to be a disilazane compound represented by the following formula:

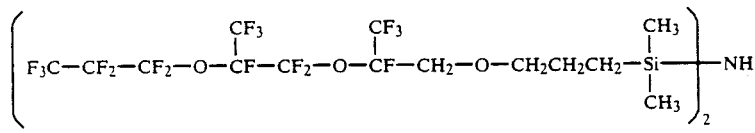

EXAMPLE 2

Example 1 was repeated to carry out the reaction, but by using a solution obtained by dissolving in 300 ml of Freon-133, 39.6 g (87 mmol) of a fluorine-containing chlorosilane compound represented by the following formula:

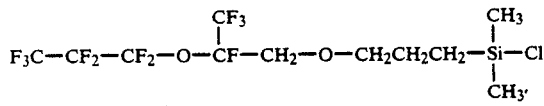

and the resulting reaction product was subjected to distillation under reduced pressure to obtain 38.0 g of a compound as a fraction at a boiling point of 140° to 143° C./2 mmHg (yield: 83%). The resulting compound was subjected to elementary analysis and GC-MS analysis, and also infrared absorption spectrum and $^1$H-NMR spectrum were measured, to obtain the following results.

|  | Elementary analysis: | | | | |
| --- | --- | --- | --- | --- | --- |
|  | C | H | N | Si | F |
| Calculated*: (%) | 31.25 | 3.46 | 1.66 | 6.64 | 49.43 |
| Found: (%) | 31.03 | 3.51 | 1.61 | 6.59 | 49.22 |

(*as C$_{22}$F$_{22}$H$_{29}$NO$_4$Si$_2$)

Figure 2:
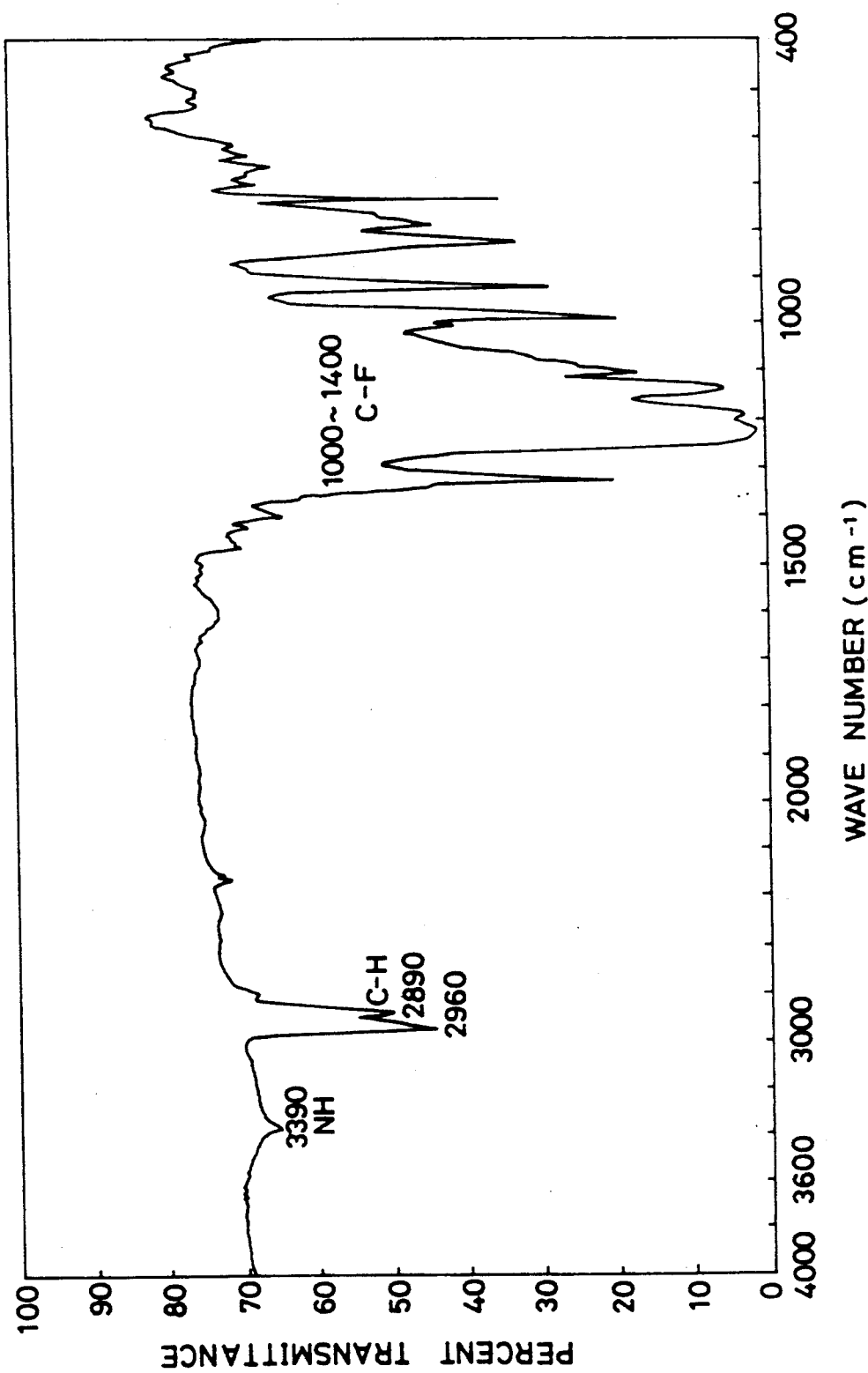

GC-MS: m/e(M+) Molecular weight: 845.
Infrared absorption spectrum:
As shown in FIG. 2, a peak derived from a —NH group was observed at a wave number of 3,390 cm$^{-1}$.
$^1$H-NMR spectrum: Solvent: Freon-113; external standard: TMS. δ (ppm): 3.90 (d, 4H, J$_{HF}$=12.0 Hz, 2×—CF—CH$_2$—O—) 3.47 (t, 4H, J=6.8 Hz, 2×—O—CH$_2$—CH$_2$—) 0.30 to 0.70 (m, 4H, 2×—CH$_2$—Si) 0.00 (s, 12H, 2×Si(CH$_3$)$_2$).

From the above results, the compound obtained was found to be a disilazane compound represented by the following formula:

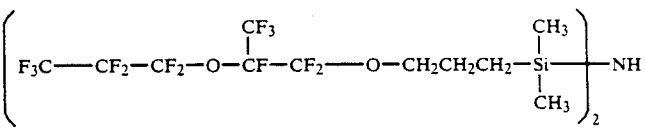

EXAMPLE 3

Example 1 was repeated to carry out the reaction, but by using a solution obtained by dissolving in 150 ml of Freon-133, 30 g (45 mmol) of a fluorine-containing chlorosilane compound represented by the following formula:

$$F_3C-CF_2-CF_2-O-\overset{\underset{|}{CF_3}}{CF}-CF_2-O-\overset{\underset{|}{CF_3}}{CF}-CF_2-O-CH_2CH_2CH_2-Si\overset{CH_3}{\underset{CH_3}{\diagdown}}Cl$$

and the resulting reaction product was subjected to distillation under reduced pressure to obtain 23 g of a compound as a fraction at a boiling point of 165° to 168° C./2 mmHg (yield: 81%). The resulting compound was subjected to elementary analysis and GC-MS analysis, and also infrared absorption spectrum and $^1$H-NMR spectrum were measured, to obtain the following results.

|  | Elementary analysis: | | | | |
| --- | --- | --- | --- | --- | --- |
|  | C | H | N | Si | F |
| Calculated*: (%) | 26.91 | 2.02 | 1.12 | 4.50 | 57.77 |
| Found: (%) | 26.58 | 1.98 | 1.15 | 4.41 | 57.69 |

(*as C$_{28}$F$_{38}$H$_{25}$NO$_6$Si$_2$)

Figure 3:
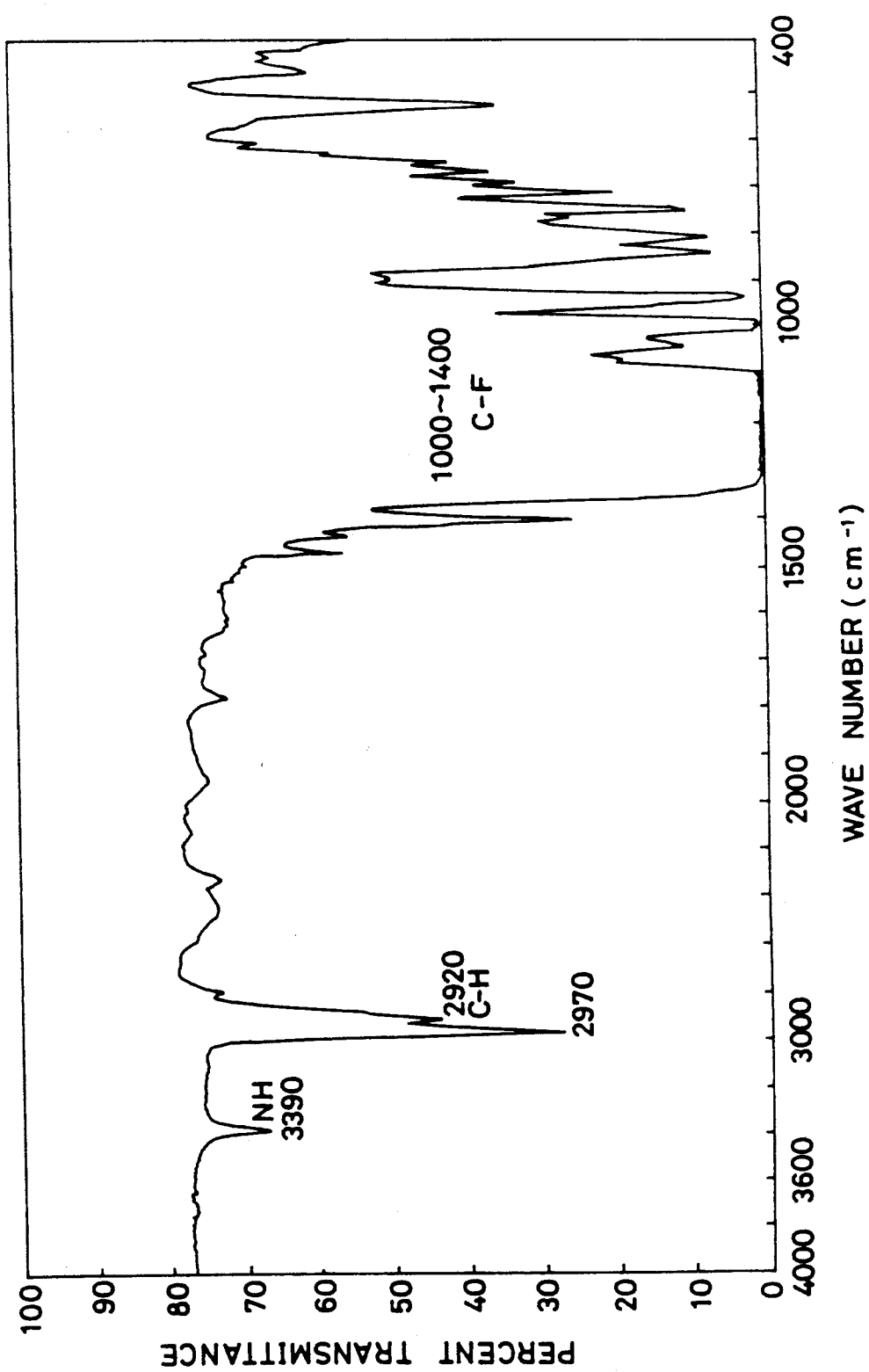

GC-MS: m/e(M+) Molecular weight: 1,249.
Infrared absorption spectrum:
As shown in FIG. 3, a peak derived from a —NH group was observed at a wave number of 3,390 cm$^{-1}$.
$^1$H-NMR spectrum: Solvent: Freon-113; external standard: TMS. δ (ppm): 3.88 (t, 4H, J=6.8 Hz, 2×—O—CH$_2$—CH$_2$—) 1.33 to 1.93 (m, 4H, 2×—CH$_2$CH$_2$CH$_2$) 0.26 to 0.67 (m, 4H, 2×CH$_2$Si) 0.00 (s, 12H, 2×Si(CH$_3$)$_2$).

From the above results, the compound obtained was found to be a disilazane compound represented by the following formula:

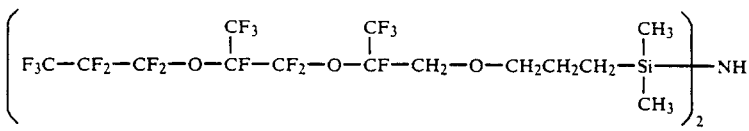

EXAMPLE 4

Example 1 was repeated to carry out the reaction, but by using a solution obtained by dissolving in 150 ml of Freon-133, 25.1 g (25 mmol) of a fluorine-containing chlorosilane compound represented by the following formula:

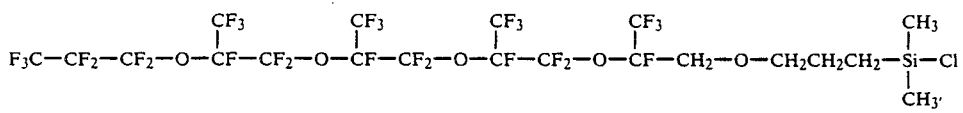

and the resulting reaction product was subjected to removal of solvent under reduced pressure to obtain 23.3 g of a highly viscous compound (yield: 91%; purity: 96%). The resulting compound was subjected to GC-MS analysis, and also infrared absorption spectrum and $^1$H-NMR spectrum were measured, to obtain the following results.

GC-MS: m/e(M+) Molecular weight: 1,955.
Infrared absorption spectrum:
A peak derived from a —NH group was observed at a wave number of 3,390 cm$^{-1}$.

$^1$H-NMR spectrum: Solvent: Freon-113; external standard: TMS. δ (ppm): 3.82 (d, 4H, $J_{HF}$=12.0 Hz, 2×—CF—C$\underline{H_2}$—O—) 3.35 (t, 4H, J=6.8 Hz, 2×—O—C$\underline{H_2}$—CH$_2$—) 1.15 to 1.83 (m, 4H, 2×—CH$_2$C$\underline{H_2}$CH$_2$) 0.20 to 0.66 (m, 4H, 2×C$\underline{H_2}$Si) 0.00 (s, 12$\overline{H, 2}$×Si(CH$_3$)$_2$).

From the above results, the compound obtained was found to be a disilazane compound represented by the following formula:

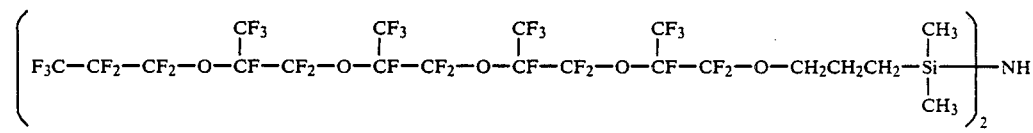

EXAMPLE 5

Example 1 was repeated to carry out the reaction, but by using a solution obtained by dissolving in 150 ml of Freon-133, 26.0 g (25 mmol) of a fluorine-containing chlorosilane compound represented by the following formula:

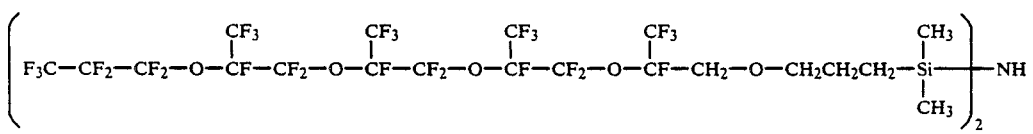

and the resulting reaction product was subjected to removal of solvent under reduced pressure to obtain 25.0 g of a compound (yield: 93%; purity: 94%). The resulting compound was subjected to GC-MS analysis, and also infrared absorption spectrum and $^1$H-NMR spectrum were measured, to obtain the following results.

GC-MS: m/e(M+) Molecular weight: 1,955.
Infrared absorption spectrum:
A peak derived from a —NH group was observed at a wave number of 3,390 cm$^{-1}$.

$^1$H-NMR spectrum: Solvent: Freon-113; external standard: TMS. δ (ppm): 3.87 (t, 4H, J=6.8 Hz, 2×—O—C$\underline{H_2}$—CH$_2$—) 1.33 to 1.93 (m, 4H, 2×—CH$_2$C$\underline{H_2}$CH$_2$) 0.25 to 0.66 (m, 4H, 2×C$\underline{H_2}$Si) 0.00 (s, 12$\overline{H, 2}$×Si(CH$_3$)$_2$).

From the above results, the compound obtained was found to be a disilazane compound represented by the following formula:

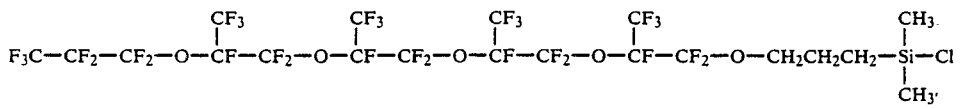

We claim:
1. A fluorine-containing organosilicon compound represented by Formula (I):

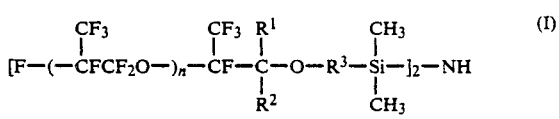

wherein n represents an integer from 1 to 4, R$^1$ and R$^2$ may be the same or different and each represent a hydrogen atom or a fluorine atom, and R$^3$ represents an alkylene group having 1 to 6 carbon atoms.

2. The compound of claim 1, wherein R$^3$ in Formula (I) comprises an alkylene selected from the group consisting of trimethylene and tetramethylene.

* * * * *